United States Patent

Zanker et al.

Patent Number: 4,810,799
Date of Patent: Mar. 7, 1989

[54] PREPARATION OF N-(3,5-DICHLOROPHENYL)OXAZOLIDINE-2,4-DIONES

[75] Inventors: Fritz Zanker, Worms; Rainer Ohlinger, Heidelberg, both of Fed. Rep. of Germany

[73] Assignee: BASF Aktiengesellschaft, Ludwigshafen, Fed. Rep. of Germany

[21] Appl. No.: 631,183

[22] Filed: Jul. 16, 1984

[30] Foreign Application Priority Data

Jul. 16, 1983 [DE] Fed. Rep. of Germany ....... 3325734

[51] Int. Cl.⁴ .................................... C07D 263/44
[52] U.S. Cl. ................................. 548/226; 548/227
[58] Field of Search ............................... 548/226

[56] References Cited

U.S. PATENT DOCUMENTS 3,366,750 6/1976 Mangold et al. ............... 548/226
4,220,787 9/1980 Scholz ........................... 548/226

FOREIGN PATENT DOCUMENTS 0038007 4/1981 European Pat. Off. ............ 548/226
2324591 12/1974 Fed. Rep. of Germany ...... 548/226

Primary Examiner—Sharon A. Gibson
Attorney, Agent, or Firm—Keil & Weinkauf

[57] ABSTRACT

N-(3,5-Dichlorophenyl)-oxazolidine-2,4-diones of the formula

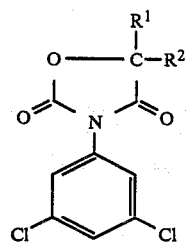

where $R^1$ is haloalkenyl, alkenyl, chloromethyl, CN, CO—O-alkyl, alkoxyalkyl or alkylthioalkyl and $R^2$ is haloalkenyl, alkenyl, hydrogen or alkyl, are prepared by a process in which 3,5-dichlorophenyl isocyanate is reacted with a glycolate of the formula

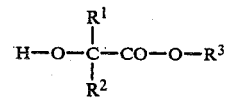

where $R^1$ and $R^2$ have the above meanings and $R^3$ is alkyl or cyclohexyl, in the presence of a tin(II) salt of the formula

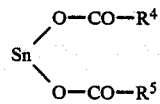

where $R^4$ and $R^5$ are identical or different and are each hydrogen, alkyl, alkenyl or unsubstituted or alkyl-substituted cycloalkyl, or benzyl or phenyl, or $R^4$ and $R^5$ together form —CH$_2$—CH$_2$—, —CH=CH— or o-phenylene, at from 0° to 110° C., the product is heated in the presence of an alcohol of the formula $R^6$—OH where $R^6$ is alkyl, hydroxyethyl or cyclohexyl, and of a basic compound, the N-(3,5-dichlorophenyl)-oxazolidine-2,4-dione precipitated from the reaction mixture is isolated by filtration at from −30° to +90° C., and additional amounts of N-(3,5-dichlorophenyl)-oxazolidine-2,4-dione are precipitated from the mother liquor by adding water, and are isolated from the aqueous liquid at from −10° to +60° C.

5 Claims, No Drawings

PREPARATION OF N-(3,5-DICHLOROPHENYL)OXAZOLIDINE-2,4-DIONES

The present invention relates to a process for the preparation of N-(3,5-dichlorophenyl)-oxazolidine-2,4-diones, in which, in the first synthesis step, an N-(3,5-dichlorophenyl)-carbamyloxyacetate is prepared in the presence of a tin(II) salt of a carboxylic acid, and additional amounts of N-(3,5-dichlorophenyl)-oxazolidine-2,4-dione are separated off from the alcoholic mother liquor by precipitation with water.

It has been disclosed that N-(3,5-dichlorophenyl)-oxazolidine-2,4-diones can be prepared in two synthesis steps. In the first step, 3,5-dichlorophenyl isocyanate (3,5-DCI) and a glycolate are reacted to give an N-(3,5-dichlorophenyl)-carbamyloxyacetate, which is cyclized in a second step, in an alcohol and in the presence of a base, to give an N-(3,5-dichlorophenyl)-oxazolidine-2,4-dione (DE-A-30 14 119). The N-(3,5-dichlorophenyl)-oxazolidine-2,4-diones are obtained in solid form and are isolated from the mother liquor in a conventional manner, for example by filtration.

The conventional reaction of equimolar amounts of 3,5-DCI and a glycolate gives a mixture of 85–90% of an N-(3,5-dichlorophenyl)-carbamyloxyacetate (I) and 10–15% of an N,N'-bis-(3,5-dichlorophenyl)-allophanate (II), the percentages being based on 3,5-DCI employed. Both the N-(3,5-dichlorophenyl)-carbamyloxyacetate and the N,N'-bis-(3,5-dichlorophenyl)-allophanate undergo cyclization in the presence of a basic catalyst to give an N-(3,5-dichlorophenyl)-oxazolidine-2,4-dione (III), this product being obtained in a yield of about 90%, based on 3,5-DCI employed, in the case of the above mixture.

The preparation of an N-(3,5-dichlorophenyl)-oxazolidine-2,4-dione from 3,5-DCI and a glycolate is illustrated below by means of equations for the reaction of 3,5-DCI with i-butyl vinyllactate:

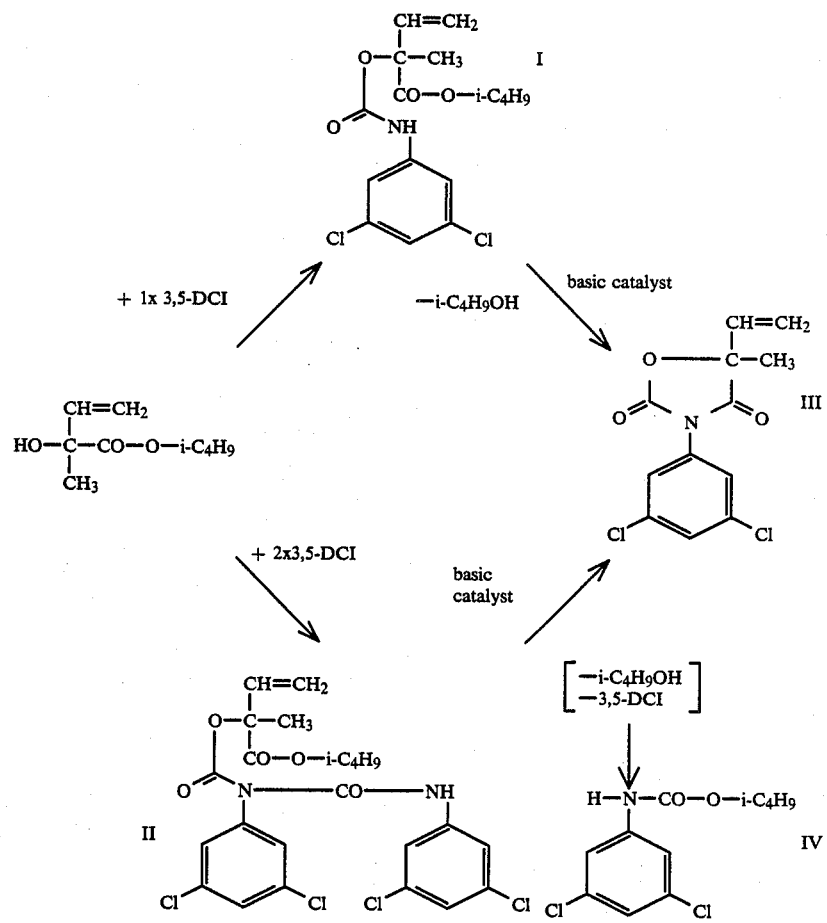

It can be seen that, in order to form one mole of N,N'-bis-(3,5-dichlorophenyl)-allophanate (II) per mole of glycolate, it is necessary to use 2 moles of 3,5-DCI, of which only one mole reacts further, in the base-catalyzed cyclization, to give the desired N-(3,5-dichlorophenyl)-oxazolidine-2,4-dione (III), while the other mole of 3,5-DCI reacts with the alcohol derived from the glycolate to give the alkyl N-(3,5-dichlorophenyl)-carbamate IV via the allophanic acid derivative II, and is therefore not available for the preparation of the oxazolidine III. When the starting materials glycolate and 3,5-DCI are used in a molar ratio of 1:1, however, formation of the allophanate derivative II takes place with the loss (for the preparation of the oxazolidine-2,4-dione) of not only 1 mole of 3,5-DCI but also 1 mole of glycolate, which does not participate in the chemical reaction.

The yield of N-(3,5-dichlorophenyl)-oxazolidine-2,4-dione is thus greatly reduced as a result of the formation of the N,N'-bis-(3,5-dichlorophenyl)-allophanate.

DE-A-23 24 591 discloses that the preparation of N-(3,5-dichlorophenyl)-carbamyloxyacetates can be carried out using about 1.5%, based on 3,5-DCI employed, of dibutyl-tin diacetate, ie. a salt of tetravalent tin, as a catalyst. If dibutyl-tin diacetate is replaced by dibutyltin dilaurate as a catalyst, the yield of N-(3,5-dichlorophenyl)-oxazolidine-2,4-diones is not increased above 90%. In DE-A-22 07 576, where the reaction is carried out without a catalyst, the yield of N-(3,5-dichlorophenyl)-oxazolidine-2,4-dione achieved is actually higher than in DE-A-23 24 591, although the yields in both cases are lower than 90%.

When the reaction is carried out as described in DE-A-30 14 119, the N-(3,5-dichlorophenyl)-oxazolidine-2,4-diones are obtained in solid form in an alcoholic mother liquor, from which they are isolated by, for example, filtration. The mother liquors contain further amounts of dissolved N-(3,5-dichlorophenyl)-oxazolidine-2,4-diones. Because they also contain substantial amounts of alkyl N-(3,5-dichlorophenyl)-carbamates and unreacted glycolates, isolation of the N-(3,5-dichlorophenyl)-oxazolidine dissolved in the mother liquor is very difficult. For example, precipitation of the N-(3,5-dichlorophenyl)-oxazolidine-2,4-dione from the mother liquor with water results in the formation of N-(3,5-dichlorophenyl)-oxazolidine-2,4-dione-containing greases or greasy solids which are very difficult to separate off and lead to blockage of the filter, which is difficult to eliminate. Substantial difficulties and product losses are involved in working up the greasy filter residues to give N-(3,5-dichlorophenyl)-oxazolidine-2,4-diones of technical-grade purity. Isolation of N-(3,5-dichlorophenyl)-oxazolidine-2,4-diones from the mother liquors is therefore not reasonable industrially.

We have found that N-(3,5-dichlorophenyl)-oxazolidine-2,4-diones of the formula

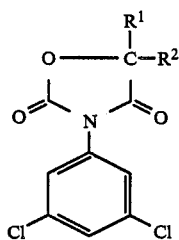

where $R^1$ is haloalkenyl or alkenyl, each of 2 to 4 carbon atoms, chloromethyl, CN, CO—O—alkyl of 2 to 5 carbon atoms, or alkoxyalkyl or alkylthioalkyl, each of 2 to 4 carbon atoms, and $R^2$ is haloalkenyl or alkenyl, each of 2 to 4 carbon atoms, hydrogen or alkyl of 1 to 4 carbon atoms, are obtained in high yield if 3,5-DCI is reacted with a glycolate of the formula

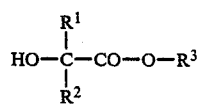

where $R^1$ and $R^2$ have the above meanings and $R^3$ is alkyl of 1 to 10 carbon atoms or cyclohexyl, in the presence of a tin(II) salt of the formula

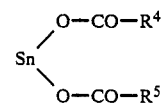

where $R^4$ and $R^5$ are identical or different and are each hydrogen, alkyl of 1 to 17 carbon atoms, alkenyl of 2 to 17 carbon atoms, unsubstituted or alkyl-substituted cycloalkyl of 5 to 12 carbon atoms or benzyl, or phenyl which is unsubstituted or monosubstituted or disubstituted by alkyl, or $R^4$ and $R^5$ together form —CH$_2$—CH$_2$—, —CH═CH— or o-phenylene, at from 0° to 110° C., the product is heated in the presence of an alcohol of the formula $R^6$—OH where $R^6$ is alkyl of 1 to 10 carbon atoms, hydroxyethyl or cyclohexyl and $R^3$ and $R^6$ are identical or different, and of a basic catalyst, the N-(3,5-dichlorophenyl)-oxazolidine-2,4-dione precipitated from the reaction mixture is isolated from the mother liquor at from −30° to +90° C., and additional amounts of N-(3,5-dichlorophenyl)-oxazolidine-2,4-dione are precipitated from the alcoholic mother liquor by adding water, and are isolated from the aqueous liquid at from −10° to +60° C.

$R^1$ is preferably vinyl or methoxymethyl, $R^2$ is preferably methyl, $R^3$ and $R^6$ are each preferably alkyl of 1 to 4 carbon atoms, eg. ethyl, n-propyl, i-propyl, n-butyl, sec.-butyl or tert.-butyl, in particular methyl or i-butyl, and $R^4$ and $R^5$ are each preferably alkyl, eg. methyl, undecyl, pentadecyl or heptadecyl, in particular heptyl, alkenyl, eg. heptadecenyl, or cycloalkyl, eg. cyclohexyl.

As a result of adding tin(II) salts in accordance with the process of the invention, the conversion to the N-(3,5-dichlorophenyl)-carbamyloxyacetates when stoichiometric amounts of 3,5-DCI and glycolate are used increases from 89–91% in the absence of a tin salt, as described in DE-A-30 14 119, to about 96%, the percentages being based on 3,5-DCI used; accordingly, the amount of undesirable N,N'-bis-(3,5-dichlorophenyl)-allophanates formed falls from 10–15% to about 2%, based on 3,5-DCI used. As a result, the yield of N-(3,5-dichlorophenyl)-oxazolidine-2,4-dione increases from about 90 to about 96% without the mother liquor being worked up, and the total yield, ie. after the mother liquor has been worked up, increases to about 98%, based on 3,5-DCI used. The procedure is carried out under atmospheric pressure (1 bar) or superatmospheric pressure (from 1 to 10 bar) at from 0° to 110° C, preferably from 10° to 90° C.

In comparison with the conventional process (DE-A-30 14 119), which takes place optimally at about 120° C., the process according to the invention is substantially less energy-consumptive since it is carried out at a lower temperature.

The tin(II) salt of a carboxylic acid is used in an amount of from 0.001 to 1, in particular from 0.005 to 0.5, % by weight, based on 3,5-DCI used.

3,5-DCI and the glycolate are used in a molar ratio of from 1.0:0.95 to 0.95:1, preferably 1:1. Since the reaction takes place rapidly even at moderately elevated temperatures, the reactants can be mixed continuously in a mixing nozzle in the presence of a catalytic amount of a tin(II) salt of a carboxylic acid, which advantageously has been mixed with one of the reactants. However, the reaction can also be carried out batchwise, for example by feeding molten 3,5-DCI into a mixture of the glycolate with a catalytic amount of a tin(II) salt of a carboxylic acid in a stirred vessel.

Advantageously, the reaction of 3,5-DCI and a glycolate to give an N-(3,5-dichlorophenyl)-carbamyloxyacetate, which is catalyzed by a tin(II) salt of a carboxylic acid, is carried out in the absence of a solvent.

However, it can also be carried out in the presence of aprotic organic solvents, such as unsubstituted, alkyl-substituted or chlorine-substituted aromatic hydrocarbons, aliphatic or cycloaliphatic hydrocarbons, esters, such as ethyl acetate, ethers, such as diethyl ether, cyclic ethers, such as tetrahydrofuran, acetonitrile or dimethylformamide, or mixtures of these solvents. However, the use of a solvent has no advantages in the further processing to N-(3,5-dichlorophenyl)-oxazolidine-2,4-diones, since this processing is effected by a conventional method and is advantageously carried out in alcohol, so that it would be necessary to remove the aprotic solvent in an expensive procedure before further processing the N-(3,5-dichlorophenyl)-carbamyloxyacetates to N-(3,5-dichlorophenyl)-oxazolidine-2,4-diones.

A great advantage of the process according to the invention is that the alcoholic mother liquors of the N-(3,5-dichlorophenyl)-oxazolidine-2,4-diones contain only small amounts of impurities which are not troublesome in the simple procedure for recovering the N-(3,5-dichlorophenyl)-oxazolidine-2,4-diones dissolved in the mother liquors by precipitation with water and filtration. Only as a result of this has it become reasonable industrially to work up the mother liquors. The latter are stirred, at from $-10°$ to $+60°$ C., in particular from $+10°$ to $+40°$ C., with water, advantageously in a volume ratio of from 1:10 to 10:1, in particular from 1:3 to 3:1, and the precipitated N-(3,5-dichlorophenyl)-oxazolidine-2,4-diones are filtered off under suction. In this way, it is possible to obtain an additional amount of about 2% of N-(3,5-dichlorophenyl)-oxazolidine-2,4-diones. These, unlike mother liquors obtained in conventional processes, contain virtually none of the above impurities, and are of a purity which meets technical and commercial requirements.

The use of water as a precipitating agent for the N-(3,5-dichlorophenyl)-oxazolidine-2,4-diones in the alcoholic mother liquors, and the ease with which the precipitated N-(3,5-dichlorophenyl)-oxazolidine-2,4-diones can be filtered, permit their isolation to be integrated into the standard production process involving batches of N-(3,5-dichlorophenyl)-oxazolidine-2,4-diones in the following manner. The N-(3,5-dichlorophenyl)-oxaozlidine-2,4-dione precipitated with water and originating from the mother liquor of the preceding batch is filtered off under suction and washed with an alcohol of the formula $R^6$—OH, after which it remains on the suction filter. The wash alcohol is discarded. The alcoholic suspension of the N-(3,5-dichlorophenyl)-oxazolidine-2,4-dione in the mother liquor of the current batch is introduced into the filter, filtered under suction and washed with a small amount of an alcohol of the formula $R^6$—OH. The mother liquor and the wash alcohol are combined, and subsequently diluted with water. The suction filter contains the N-(3,5-dichlorophenyl)-oxazolidine-2,4-dione from the current charge combined with that obtained from working up the mother liquor of the preceding charge. The contents of the suction filter are washed with water and removed from the filter, and the wash water is discarded. Isolating the valuable N-(3,5-dichlorophenyl)-oxazolidine-2,4-diones from the mother liquor by the process of the invention while dispensing with the conventional recovery of the alcohols $R^3$—OH and $R^6$—OH from the mother liquors has a substantial advantage because the yield of end product is increased and, in comparison, the loss of alcohols can be neglected.

The Examples which follow illustrate the process according to the invention. Parts are by weight, and parts by weight bear the same relation to parts by volume as that of the kilogram to the liter.

EXAMPLE 1

160 parts of liquid 3,5-DCI (mp. 30°–31° C.) at 40° C. were added to a mixture of 146.2 parts of i-butyl vinyllactate and 0.1 part of tin dilaurate in the course of 10 minutes at such a rate that the reaction temperature increased from 35° to 90° C. The mixture was cooled to 80° C., stirring was continued at this temperature for 2 hours and the mixture was then cooled to 70° C. A solution of 7 parts of tri-n-propylamine in 200 parts by volume of methanol was then added, after which the mixture was kept at 70° C. for 5 hours and then cooled to room temperature. The precipitated N-(3,5-dichlorophenyl)-5-methyl-5-vinyloxazolidine-2,4-dione was filtered off under suction, washed with twice 30 parts by volume of methanol and dried. Yield: 229.5 parts, corresponding to 94.3% of theory, based on 3,5-DCI used. Mp.: 107°–108° C.

200 parts of water were added to the mother liquor obtained after the N-(3,5-dichlorophenyl)-5-methyl-5-vinyloxazolidine-2,4-dione had been filtered off under suction, and the temperature was kept below 40° C. The product was filtered off under suction, washed with 15 parts of methanol and dried. Yield: 6.2 parts (2.5% of theory, based on 3,5-DCI used) of N-(3,5-dichlorophenyl)-5-methyl-5-vinyloxazolidine-2,4-dione of melting point 105°–107° C.

EXAMPLE 2

160 parts of 3,5-DCI were added to a mixture of 146.2 parts of butyl vinyllactate and 0.1 part of tin diacetate at 60° C. On heating to 65° C., a strongly exothermic reaction took place, with the result that the reaction mixture warmed up to 90° C. The mixture was kept at this temperature for 3 hours, cooled to 70° C. and poured into a solution of 6 parts of triethylamine in 200 parts by volume of methanol, and the resulting mixture was kept at 70° C. for 5 hours and then cooled to 20° C. The mixture was filtered under suction and the residue was washed with twice 30 parts by volume of methanol and dried. Yield: 228.5 parts (93.9% of theory, based on 3,5-DCI used) of N-(3,5-dichlorophenyl)-5-methyl-5-vinyloxazolidine-2,4-dione of melting point 106°–108° C.

The mother liquor (at 30° C.) was poured into 300 parts of water, the mixture was filtered under suction and the residue was washed with 12 parts of methanol and dried. Yield: 6 parts (2.5% of theory, based on 3,5-DCI used) of N-(3,5-dichlorophenyl)-5-methyl-5-vinyloxazolidine-2,4-dione of melting point 104°–107° C.

EXAMPLE 3

160 parts of molten 3,5-DCI at 40° C. were added to a solution of 0.05 part of tin dioctoate and 160.7 parts of i-butyl methoxymethyllactate at 80° C. in the course of 60 minutes. This reaction mixture was stirred for a further 2 hours at 80° C., after which it was run into a solution of 5 parts of triethylamine in 180 parts by volume of methanol. The mixture was kept at 70° C. for 5 hours and then cooled to 20° C., after which it was filtered under suction and the residue was washed with twice 25 parts of methanol and dried. Yield: 245 parts (94.7% of theory, based on 3,5-DCI used) of N-(3,5-dichlorophenyl)-5-methyl-5-methoxymethyloxazolidine-2,4-dione of melting point 111°–113° C.

350 parts of water were added, at 25° C., to the mother liquor obtained after the N-(3,5-dichlorophenyl)-5-methyl-5-methoxymethyloxazolidine-2,4-dione had been filtered off under suction. The resulting mixture was filtered under suction and the residue was washed with 15 parts of methanol and dried. Yield: 5.7 parts (2.2% of theory, based on 3,5-DCI used) of N-(3,5-dichlorophenyl)-5-methyl-5-methoxymethyloxazolidine-2,4-dione of melting point 108°–111° C.

EXAMPLE 4

147 parts of i-butyl vinyllactate were added to a solution of 0.05 part of tin dioctoate and 160 parts of 3,5-DCI at 60° C. in the course of 5 minutes. Stirring was continued for 4 hours at 60° C., after which a solution of 7 parts of tri-n-propylamine in 200 parts by volume of methanol was added at this temperature. The mixture was kept at 70° C. for 5 hours and then cooled to 20° C., and the precipitated N-(3,5-dichlorophenyl)-5-methyl-5-vinyloxazolidine-2,4-dione was filtered off under suction, washed with twice 20 parts by volume of methanol and dried. Yield: 234 parts, corresponding to 96.1% of theory, based on 3,5-DCI used. Mp.: 107°–108° C.

350 parts of water were added, at 25° C., to the mother liquor obtained after the N-(3,5-dichlorophenyl)-5-methyl-5-vinyloxazolidine-2,4-dione had been filtered off under suction. The precipitated N-(3,5-dichlorophenyl)-oxazolidine-2,4-dione was filtered off under suction, washed with twice 10 parts of methanol and dried. Yield: 5.6 parts, corresponding to 2.3% of theory, based on 3,5-DCI used. Mp.: 105°–107° C.

EXAMPLE 5

2,500 parts of molten 3,5-DCI at 50° C. were run into a solution, at 20° C., of 0.5 part of tin dioctoate in 2,287 parts of i-butyl vinyllactate in the course of 2 hours at a rate such that the reaction temperature increased from 20° to 80° C. The mixture was kept at 80° C. for 2 hours and then run into a solution of 110 parts of tripropylamine in 3,200 parts by volume of methanol, the methanolic reaction solution boiling gently. The mixture was refluxed for 4 hours and then cooled to below 20° C., and the precipitate which separated out was filtered off under suction and washed with 300 parts by volume of methanol. The mother liquor and the wash methanol were combined. The contents of the suction filter were washed with a further 10,000 parts of water and sucked thoroughly dry, and the suction filter was then emptied. Yield, based on dry weight: 3,600 parts (94.6% of theory, based on 3,5-DCI used) of N-(3,5-dichlorophenyl)-5-methyl-5-vinyloxazolidine-2,4-dione. The wash water was discarded.

3,000 parts of water were added to the stirred mixture of wash methanol and mother liquor, the temperature not exceeding 35° C. The resulting precipitate was filtered off under suction over the above, emptied suction filter, and was washed with 50 parts of methanol. The aqueous filtrates and the wash methanol were discarded. The methanol-moist precipitate contained on average 80 parts of solid N-(3,5-dichlorophenyl)-5-methyl-5-vinyloxazolidine-2,4-dione, corresponding to a yield of 2.1% of theory, based on 3,5-DCI used. In continuous batch operation, it was not removed but was stirred, on the suction filter, with the methanolic slurry of N-(3,5-dichlorophenyl)-5-methyl-5-vinyloxazolidine-2,4-dione from the subsequent batch, and the resulting slurry was filtered under suction. The residue was washed, as described above, with 300 parts by volume of methanol and 10,000 parts of water, filtered off under suction and discharged. A mixture of wash methanol and mother liquor was once again obtained, and was worked up as described above. In this manner, a water-moist filtration residue consisting of 3,680 parts (3,600+80), based on dry weight, of N-(3,5-dichlorophenyl)-5-methyl-5-vinyloxazolidine-2,4-dione was obtained, corresponding to a yield of 96.7%, based on 3,5-DCI used. The melting point of the dry product was 106°–108° C.

We claim:

1. A process for the preparation of an N-(3,5-dichlorophenyl)-oxazolidine-2,4-dione of the formula

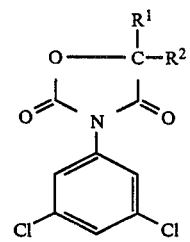

where $R^1$ is haloalkenyl or alkenyl, each of 2 to 4 carbon atoms, chloromethyl, CN, CO—O—alkyl of 2 to 5 carbon atoms, or alkoxyalkyl or alkylthioalkyl, each of 2 to 4 carbon atoms, and $R^2$ is haloalkenyl or alkenyl, each of 2 to 4 carbon atoms, hydrogen or alkyl of 1 to 4 carbon atoms, wherein 3,5-dichlorophenyl isocyanate is reacted with a glycolate of the formula

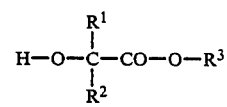

where $R^1$ and $R^2$ have the above meanings and $R^3$ is alkyl of 1 to 10 carbon atoms or cyclohexyl, in the presence of a tin(II) salt of the formula

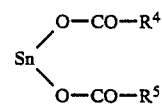

where $R^4$ and $R^5$ are identical or different and are each hydrogen, alkyl of 1 to 17 carbon atoms, alkenyl of 2 to 17 carbon atoms, unsubstituted or alkyl-substituted cycloalkyl of 5 to 12 carbon atoms or benzyl, or phenyl which is unsubstituted or monosubstituted or disubstituted by alkyl, or $R^4$ and $R^5$ together form —CH$_2$—CH$_2$—, —CH=CH— or o-phenylene, at from 0° to 110° C., the batch is heated in the presence of an alcohol of the formula $R^6$—OH where $R^6$ is alkyl of 1 to 10 carbon atoms, hydroxyethyl or cyclohexyl and $R^3$ and $R^6$ are identical or different, and a basic catalyst, the N-(3,5-dichlorophenyl)-oxazolidine-2,4-dione precipitated from the reaction mixture is isolated from the mother liquor at from $-30°$ to $+90°$ C., and additional amounts of N-(3,5-dichlorophenyl)-oxazolidine-2,4-dione are precipitated from the alcoholic mother liquor by adding water, and are isolated from the aqueous liquid at from $-10°$ to $+60°$ C.

2. The process of claim 1, wherein the reaction is carried out using a compound in which $R^1$ is vinyl or methoxymethyl, $R^2$ is methyl and $R^3$ is alkyl of 1 to 4 carbon atoms.

3. The process of claim 1, wherein $R^4$ and $R^5$ are each heptyl.

4. The process of claim 1, wherein the volume ratio of alcoholic mother liquor to water is from 1:3 to 3:1.

5. The process of claim 1, wherein, in batchwise production, the N-(3,5-dichlorophenyl)-oxazolidine-2,4-dione which has been separated off from the previous batch by adding water and has been filtered off is mixed, on the filter unit, with the mixture of mother liquor and N-(3,5-dichlorophenyl)-oxazolidine-2,4-dione from the current batch, and the combined product is isolated from the mother liquor of the current batch by filtration.

* * * * *